United States Patent [19]

Zeiss

[11] Patent Number: 5,374,736

[45] Date of Patent: Dec. 20, 1994

[54] L-4-(PHOSPHINYLETHYL)-1,3-OXAZOLI-DIN-5-ONE DERIVATIVES AS INTERMEDIATES FOR SYNTHESIS OF PHOSPHORUS-CONTAINING L-AMINO ACIDS

[75] Inventor: Hans-Joachim Zeiss, Sulzbach, Germany

[73] Assignee: Hoechst Aktiengesellschaft, Frankfurt am Main, Germany

[21] Appl. No.: 17,405

[22] Filed: Feb. 12, 1993

Related U.S. Application Data

[63] Continuation of Ser. No. 356,799, May 25, 1989, abandoned.

[30] Foreign Application Priority Data

May 27, 1988 [DE] Germany .................... 3817956

[51] Int. Cl.[5] .......................... C07D 263/32
[52] U.S. Cl. .......................... 548/119
[58] Field of Search .......................... 548/119

[56] References Cited

U.S. PATENT DOCUMENTS

| | | | |
|---|---|---|---|
| 3,798,230 | 3/1974 | Beutel et al. | 558/17 |
| 3,798,230 | 2/1971 | Beutel et al. | 260/307 |
| 3,956,305 | 5/1976 | Mudd | 548/119 |
| 4,176,121 | 11/1979 | Gutman | 548/119 |
| 4,212,861 | 7/1980 | Theobald et al. | 548/119 |
| 4,226,941 | 10/1980 | Goi et al. | 435/280 |
| 4,265,654 | 5/1981 | Takematsu et al. | 71/86 |
| 4,389,488 | 6/1983 | Grabley et al. | 435/280 |
| 4,499,027 | 2/1985 | Minowa et al. | 71/86 |
| 4,594,199 | 6/1986 | Thottahil | 558/137 |
| 4,687,767 | 8/1987 | Bosies et al. | 548/119 |
| 4,777,279 | 10/1988 | Zeiss | 548/145 |
| 4,922,006 | 5/1990 | Zeiss | 562/11 |

FOREIGN PATENT DOCUMENTS

| | | |
|---|---|---|
| 0238954 | 9/1987 | European Pat. Off. . |
| 3525267 | 3/1986 | Germany . |
| 3609818 | 9/1987 | Germany . |

OTHER PUBLICATIONS

Bull. Chem. Soc. Jpn., vol. 60, (1987), pp. 1761–1766.
Sci. Reports of Meiji Seika Kaisha, No. 13, (1973), pp. 34–41.
J. of Antibiotics, (1983), pp. 96–98.
Jerry March, Advanced Organic Chemistry, 3rd Edition, pp. 387, 388, 789 (1985).
John D. Roberts et al., Organic Chemistry (1972) pp. 311–312.
Chem. Abstract 105:134143u (1986).
Derwent Abstract 86–082792/13 (1986).

*Primary Examiner*—Mukund J. Shah
*Assistant Examiner*—Pavanaram K. Sripada
*Attorney, Agent, or Firm*—Curtis, Morris & Safford

[57] ABSTRACT

A compound of the formula (IV)

$$R_1(O)_n - \underset{\underset{(O)_mR_2}{|}}{\overset{\overset{O}{\|}}{P}} - CH_2 - CH_2 \underset{\underset{R_3'}{\diagdown}}{\overset{\overset{O}{\diagup}}{\underset{N}{\diagdown}}} \overset{O}{\underset{R_7}{\diagup}} \quad \text{(IV)}$$

in which
R$_1$ and R$_2$, independently of one another, are hydrogen, (C$_1$–C$_6$)-alkyl which is unsubstituted, monosubstituted or polysubstituted by halogen or (C$_6$–C$_{10}$)-aryl, or are (C$_3$–C$_{10}$)-cycloalkyl,
R$_3$ is (C$_1$–C$_6$)-alkyl which is unsubstituted, monosubstituted or polysubstituted by halogen and monosubstituted by hydroxyl or which is monosubstituted by hydroxyl, or is (C$_1$–C$_{10}$)-acyl which can be monosubstituted or polysubstituted by halogen or (C$_1$–C$_6$)-alkyl, or can be monosubstituted by (C$_6$–C$_{10}$)-aryl, (C$_1$–C$_6$)-alkoxy or (C$_1$–C$_6$)-alkoxy which is substituted by (C$_6$–C$_{13}$)-aryl,
R$_7$ is hydrogen, (C$_1$–C$_5$)-alkyl which can be monosubstituted or polysubstituted by halogen,
n is the number 0 or 1, with the exception that R$_1$ is not hydrogen if n is 1, and
m is the number 0 if R$_2$ is not hydrogen, or is 1.

5 Claims, No Drawings

L-4-(PHOSPHINYLETHYL)-1,3-OXAZOLIDIN-5-ONE DERIVATIVES AS INTERMEDIATES FOR SYNTHESIS OF PHOSPHORUS-CONTAINING L-AMINO ACIDS

This application is a continuation of application Ser. No. 07/356,799, filed May 25, 1989, now abandoned.

The present invention relates to a process for the preparation of phosphorus-containing L-amino acids of the formula I or their salts

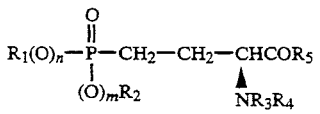

in which
R$_1$ and R$_2$ independently of one another denote hydrogen, (C$_1$–C$_6$)-alkyl which is unsubstituted, monosubstituted or polysubstituted by halogen or (C$_6$–C$_{10}$)-aryl, or (C$_3$–C$_{10}$)-cycloalkyl,
R$_3$ denotes hydrogen, (C$_1$–C$_6$)-alkyl which is unsubstituted, monosubstituted or polysubstituted by halogen and/or monosubstituted by hydroxyl, (C$_1$–C$_{10}$)-acyl which may be monosubstituted or polysubstituted by halogen or (C$_1$–C$_6$)-alkyl or monosubstituted by (C$_6$–C$_{10}$)-aryl, (C$_1$–C$_6$)-alkoxy or (C$_1$–C$_6$)-alkoxy which is substituted by (C$_6$–C$_{13}$)-aryl,
R$_4$ denotes hydrogen or a radical of the formula —CH(OH)—R$_7$ in which R$_7$ is defined as set forth in formula (III) below,
R$_5$ denotes hydroxyl, (C$_1$–C$_6$)-alkoxy, amino, Ala-Ala-OR$_6$ or Ala-Leu-OR$_6$,
R$_6$ denotes hydrogen, (C$_1$–C$_1$)-alkyl or benzyl,
n denotes the number zero or one and
m denotes the number zero if R$_2$ is not hydrogen, or 1,
which comprises reacting
a) a compound of the formula II

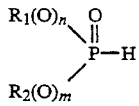

where
R$_1$ and R$_2$ have the abovementioned meaning with the exception that
R$_1$ is not hydrogen if n is 1, with a compound of the formula III

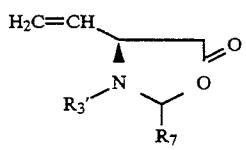

in which
R$_3'$ has the meaning of R$_3$ apart from hydrogen and
R$_7$ denotes H, (C$_1$–C$_5$)-alkyl which is unsubstituted, monosubstituted or polysubstituted by halogen, in the presence of catalytic amounts of a radical former and b) reacting the intermediate obtained of the formula IV

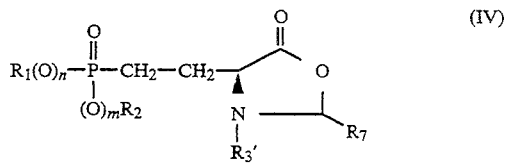

with HCl, an alkali metal hydroxide, an alkali metal alkoxide, NH$_3$, H-Ala-Ala-OR$_6$ or H-Ala-Leu-OR$_6$, where R$_6$ has the abovementioned meaning apart from hydrogen, and optionally derivatizing the compound of the formula I obtained in a customary manner.

In the above definitions, (C$_6$–C$_{10}$)-aryl is taken to mean, in particular, phenyl or naphthyl.

(C$_6$–C$_{13}$)-Aryl denotes, in particular, phenyl, naphthyl or fluorenyl. Examples of the substituted acyl radicals mentioned in connection with R$_3$ are dichloro-, trichloro- or trifluoroacetyl, benzyloxycarbonyl, fluorenylmethoxycarbonyl and naphthylmethoxycarbonyl.

The compounds of the formula I are known, for example, from Bull. Chem. Soc. Japan 60, 1761 (1987), U.S. Pat. No. DE-OS 2,856,260 and Sci. Rep. MeiJi Seika Kaisha 13, 34 (1973). Their herbicidal, fungicidal and antiviral properties are also described therein. The latter property applies specifically to L-2-amino-4-phosphonobutyric acid. In addition, L-3-amino-3-carboxypropanephosphonous acid is a useful intermediate in the preparation of the herbicides concerned by fermentation. (J. Antibiotics 36, 96 (1983)).

Amongst the compounds of the formula I, the compounds in which R$_1$(O)$_n$ denotes CH$_3$ or C$_2$H$_5$, R$_2$(O)$_m$ denotes OH, R$_3$ and R$_4$ are H and R$_5$ denotes OH, Ala-Ala-OH or Ala-Leu-OH and their salts are to be emphasized. The herbicide glufosinate (4-[hydroxy(methyl)-phosphinoyl]-homoalanine, Pesticide Manual, 8th edition (1987), p. 448) has particular significance.

According to U.S. Pat. No. DE-OS 2,856,260, the herbicidal action of the L-isomer of glufosinate is twice as large as that of the racemate. The use of the L-isomer therefore offers clear advantages.

The process according to the invention yields the L-isomer of the formula I in high optical yields of above 90%, which corresponds to a content of 95% of the L-isomer.

Phosphorus-containing L-amino acids having high optical purity can as yet only be obtained by complicated enzymatic racemate cleavage methods (U.S. Pat. No. DE-OS 2,939,269 and U.S. Pat. No. DE-OS 3,048,612).

At the same time, processes are admittedly known which make use of an enantioselective synthesis, but these have various disadvantages.

Thus for example, the enantioselective alkylation of chiral Schiff bases described in EP-OS 127,429 only gives optical yields of a maximum of 78%, while the asymmetric hydrogenation of 2,3-dehydroamino acids described in U.S. Pat. No. DE-OS 3,609,818 begins from starting materials which are accessible with difficulty.

In addition, two processes are known which begin from heterocyclic precursors (U.S. Pat. No. DE-OS 3,542,645 and U.S. Pat. No. DE-OS 3,525,267).

These processes have the disadvantage, however, that the heterocyclic starting compounds concerned can only be prepared by multi-stage complicated synthesis steps, while the starting compounds of the formula III of the process according to the invention can be prepared simply, even in an industrial production process, from the easily accessible L-glutamic acid.

Process step a) of the process according to the invention is carried out in the temperature range between 50° and 200° C, preferably between 70° and 140° C.

Possible radical formers are all the known compounds which form radicals in the temperature range from 50°-200° C.

Examples of such compounds are:

Organic peroxides such as di-tert-butyl peroxide or dibenzoyl peroxide, carboxylic acid peresters such as tert-butyl perpivalate, tert-butyl peroctoate, tert-amyl perpivalate, tert-butyl perneodecanoate or tert-amyl perneodecanoate or aliphatic azo compounds such as azobisisobutyronitrile.

Instead of chemical radical formers high energy rays leading to radical formation, such as UV, γ or X-rays can also be used. Similarly, the catalyst can consist of mixtures of two or more of the radical formers listed.

Process step a) is in general carried out by watching the unsaturated compound of the general formula III with 1- to 10-fold amount, preferably 1.5- to 4-fold excess of the phosphine compound of the general formula II to the reaction temperature without solvent or in the presence of a high-boiling, inert solvent such as toluene or xylene and adding 0.1 to 20 mol percent, but preferably 0.5 to 10 mol percent, of the radical-forming catalyst, relative to the components of the general formula III.

Another procedure consists of initially introducing the phosphine compound of the general formula II, warming to reaction temperature and adding a mixture of the unsaturated compound III and the catalyst, if appropriate dissolved in a high-boiling, inert solvent.

In order to avoid undesired side reactions, it is advisable to carry out the reaction in a protective gas atmosphere. Possible protective gases are nitrogen, argon or carbon dioxide.

After completion of the reaction, the excess phosphine component II present, if appropriate together with the solvent, is separated by known processes, such as, for example, distillation of the reaction product. The crude reaction product can be further purified by known processes such as, for example, chromatography.

Surprisingly, no radical polymerization of the substituted vinyl compound III, but a smooth reaction to give the intermediate of the formula IV, takes place under the reaction conditions described, cf. G. Henrici-Olive, S. Olive: Polymerisation, p. 1 ff, Verlag Chemie, Weinheim (1969).

In addition, it was not to be expected that a regioselective addition of the component II to the double bond of III occurs, since the formation of isomer mixtures was observed in similar reactions, see Tetrahedron Letters 1984, 4737.

It is furthermore remarkable that in spite of the relatively high reaction temperatures no racemization occurs.

The compounds of the formula III are known from Tetrahedron Letters 25, 1425 (1984) or can be prepared by the methods described therein. Their preparation is carried out from the easily accessible L-glutamic acid.

The compounds of the formula II are described in Houben-Weyl, Methoden der organischen Chemie (Methods of organic chemistry), Volume XII/1, p. 1, 5, 193 and 294 (1963), Georg-Thieme-Verlag, Stuttgart.

In process step b), the amino acids ($R_5$=OH) are obtained in the form of their hydrochlorides using HCl.

In particular, aqueous 3N–12N HCl, particularly preferably 5N–10N HCl, is used.

The compound of the formula IV is expediently dissolved in the aqueous hydrochloric acid and heated at 90° to 130° C. for several hours. The acidic aqueous solution is then extracted using a water-immiscible solvent such as toluene, xylene, dichloromethane or methyl isobutyl ketone in order to remove the products resulting from the cleavage of the radical $R_3$, $R_4$ or, if appropriate, $R_1$ or $R_2$. The aqueous solution is concentrated completely and the crude product is purified, if desired, by known measures such as recrystallization or ion exchange. If desired, the hydrochlorides of the compounds of the general formula I thus obtained can be converted into the free amino acids in a customary manner.

Surprisingly, no racemization occurs, even in process step b), although this is known for the related 1,3-oxazolin-5-one compounds (Houben-Weyl, Volume XV/1, p. 35 ff).

In order to avoid undesired side reactions, even in process step b), the reaction is advantageously carried out under a protective gas atmosphere, for example under argon, nitrogen or carbon dioxide.

The alkaline hydrolysis by means of alkali metal hydroxides such as NaOH, KOH or alkali metal alkoxides is carried out analogously to the procedure described in Chem. Pharm. Bull. 17, 1679 (1969).

The reaction of the compounds of the formula IV with ammonia, Ala-Ala-OR$_6$ or Ala-Leu-OR$_6$ is carried out in a customary manner (Houben-Weyl XV/2, p. 91 ff).

The compounds of the formula I obtained can either be converted into their salts by known methods or the radicals $R_1$, $R_2$, $R_3$, $R_4$, $R_5$ or $R_6$ can be cleaved off in a suitable manner.

Salt formation is carried out by means of methods familiar to the person skilled in the art. The salts of the compounds I are known from U.S. Pat. No. DE-OS 2,856,260.

The cleavage reactions of the radicals $R_1$, $R_2$, $R_3$, $R_4$, $R_5$ or $R_6$ are also known per se.

If $R_s$ denotes —COOCH$_2$C$_6$H$_5$ and $R_6$ denotes CH$_2$C$_6$H$_5$, cleavage takes place, for example, by catalytic hydrogenation. Cleavage of the radical $R_1$(for n=1) or $R_2$ (for m=1) takes place by means of mineral acids or specific reagents such as sodium iodide/trimethylchlorosilane in acetonitrile (Houben-Weyl E2, p. 312 ff and 322 ff) or bromotrimethylsilane (Tetrahedron Letters 1977, 155).

The intermediate compounds of the formula IV are novel and are therefore also a subject of the present invention.

The following Examples serve to illustrate the invention.

A. Preparation of the Intermediates (Process Step a))

EXAMPLE 1

L-3-Benzyloxycarbonyl-4-[2-[isoamoxy(methyl)phosphinyl]ethyl]-1,3-oxazolidin-5-one 5.0 g (0.033 mol) of isoamyl methanephosphonite are heated to 90° C. under an argon atmosphere and a solution of 2.7 g (0.011 mol) of L-3-benzyloxycarbonyl-4- vinyl-1,3-oxazolidin-5-one and 0.024 g (0.00011 mol) of tert-butyl perneodecanoate in 4 ml of xylene is added dropwise in the course of 10 min. After completion of the addition, the mixture is stirred for a further 60 min at 90° C., then the excess isoamyl methanephosphonite is distilled off in a high vacuum. The crude product is purified by chromatography on silica gel (eluent: dichloromethane/methanol). 0.8 g (18.3% of theory) of L-3-benzyloxycarbonyl-4-[2-[isoamoxy(methyl)phosphinyl]ethyl]-1,3-oxazolidin-5-one is obtained as a colorless oil.

$^{31}$P-NMR (CDCl$_3$): 52.710

$[\alpha]_D^{23}$: 74.4° (C=0.46 in CHCl$_3$)

EXAMPLE 2

L-3-Benzyloxycarbonyl-4-[2-[isobutoxy(methyl)phosphinyl]ethyl]-1,3-oxazolidin-5-one 2.0 g (0.008 mol) of L-3-benzyloxycarbonyl-4-vinyl-1,3-oxazolidin-5-one and 3.2 g (0.024 mol) of isobutyl methanephosphonite are dissolved in 6 ml of xylene and the mixture is heated to 125° C. under an argon atmosphere. 0.022 g (0.0001 mol) of tert-butyl perethylhexanoate are added dropwise to the hot reaction mixture. After 30 min and 60 min, 0.022 g (0.0001 mol) each time of tert-butyl perethylhexanoate is added dropwise again.

After the last addition, the mixture is stirred for a further 60 min at 125° C. The excess isobutyl methanephosphonite is distilled off in a high vacuum and the crude product is chromatographed on silica gel (eluent: dichloromethane/methanol). 2.20 g (71.1% of theory) of L-3-benzyloxycarbonyl-4-[2-[isobutoxy(methyl)phosphinyl]-ethyl]-1,3-oxazolidin-5-one are obtained as a colorless oil.

$^1$H-NMR (CDCl$_3$): 0.93 (d, J=7Hz, 6H), 1.43 (d, J=14Hz, 3H), 1.68-2.38 (m, 5H), 3.72 (t, J=7Hz, 2H), 4.38 (t, J=5.5Hz, 1H), 5.19 (s, 2H), 5.24 (d, J=5Hz, 1H), 5.53 (d, J=5Hz, 1H), 7.38 (s, 5H)

$^{31}$P-NMR (CDCl$_3$):52.852

$[\alpha]_D^{19.5}$: 72.6° (C=0.67 in CHCl$_3$)

C$_{18}$H$_{26}$NO$_6$P (383.373) Calculated: C 56.4; H 6.8; N 3.6 Found : C 56.3; H 6.8; N 3.6

EXAMPLE 3

L-3-Benzyloxycarbonyl-4-[2-[ethoxy(methyl)phosphinyl]-ethyl]-1,3-oxazolidin-5-one 2.0 g (0.0182 mol) of ethyl methanephosphonite are heated to 120° C. under an argon atmosphere and a solution of 1.5 g (0.006 mol) of L-3-benzyloxycarbonyl-4-vinyl-1,3-oxazolidin-5-one and 0.032 g (0.00015 mol) of tert-butyl perethylhexanoate in 4 ml of xylene is added dropwise in the course of 15 min. After completion of the addition, the mixture is stirred for a further 70 min at 120° C., then the excess ethyl methanephosphonite is distilled off in a high vacuum. The crude product is purified by chromatography on silica gel (eluent: dichloromethane/methanol). 2.1 g (97.4% of theory) of L-3-benzyloxycarbonyl-4-[2-ethoxy(methyl)-phosphinyl]ethyl]-1,3-oxazolidin-5-one are obtained as a colorless oil.

$^1$H-NMR (CDCl$_3$): 1.30 (t, J=7Hz, 3H), 1.43 (d, J=14Hz, 3H), 1.57-2.48 (m, 4H), 4.03 (quint, J=7Hz, 2H), 4.37 (t, J=5-5Hz, 1H), 5.19 (s, 2H), 5.24 (d, J=5Hz, 1H), 5.53 (d, J=5Hz, 1H), 7.40 (s, 5H)

$^{31}$P-NMR (CDCl$_3$): 52.780

$[\alpha]_D^{23}$: 79.7° (C=0.49 in CHCl$_2$)

EXAMPLE 4

L-3-Benzyloxycarbonyl-4-[2-[cyclohexyloxy(methyl)-phosphinyl]ethyl]-1,3-oxazolidin-5-one Using cyclohexyl methanephosphonite, 89.0% of theory of L-3-benzyloxycarbonyl-4-[2-[cyclohexyloxy(methyl)phosphinyl]ethyl]-1,3-oxazolidin-5-one is obtained analogously to Example 3 as a colorless oil.

$^1$H-NMR (CDCl$_3$): 1.43 (d, J=14Hz, 3H) overlaid by 1.10-2.45 (m, 14H), 4.37 (t, J=5.5Hz, 1H), 5.19 (s, 2H), 5.23 (d, J=5Hz, 1H), 5.52 (d, J=5Hz, 1H), 7.38 (s, 5H)

$^{31}$P-NMR (CDCl$_3$):51.364

$[\alpha]_D^{23}$: 69.4° (C=0.59 in CHCl$_3$)

EXAMPLE 5

L-3-Benzyloxycarbonyl-4-[2-(dimethylphosphinyl)ethyl]-1,3-oxazolidin-5-one 2.6 g (0.033 mol) of dimethylphosphane oxide are heated to 120° C. under an argon atmosphere and a solution of 2.7 g (0.011 mol) of L-3-benzyloxycarbonyl-4-vinyl-1,3-oxazolidin-5-one and 0.040 g (0.00018 mol) of tert-butyl perethylhexanoate in 4.5 ml of xylene is added dropwise in the course of 10 min.

After completion of the addition, the mixture is stirred for a further 55 min at 120° C., then the excess dimethylphosphine oxide is distilled off in a high vacuum. The crude product is purified by chromatography on silica gel (eluent: dichloromethane/methanol). 2.20 g (62.0% of theory) of L-3-benzyloxycarbonyl-4-[2-(dimethylphosphinyl)ethyl]-1,3-oxazolidin-5-one are obtained as a colorless oil.

$^1$H-NMR (CDCl$_3$): 1.44 (d, J=14Hz, 6H) overlaid by 1-30-2.50 (m, 4H), 4.35 (t, J=5.5Hz, 1H), 5.18 (s, 2H), 5.24 (d, J=5Hz, 1H), 5.50 (d, J=5Hz, 1H), 7.35 (s, 5H)

$^{31}$P-NMR (CDCl$_3$): 42.170

$[\alpha]_D^{23}$: 81.7° (C=0.4 in CHCl$_3$)

EXAMPLE 6

L-3-Benzyloxycarbonyl-4-[2-(diisopropoxyphosphinyl)ethyl]-1,3-oxazolidin-5-one 5.1 g (0.031 mol) of diisopropyl phosphite are heated to 120° C. under an argon atmosphere and a solution of 1.9 g (0.0077 mol) of L-3-benzyloxycarbonyl-4-vinyl-1,3-oxazolidin-5-one and 0.12 g (0.00055 mol) of tert-butyl perethylhexanoate in 4 ml of xylene are added dropwise in the course of 25 min. The mixture is stirred for 60 min at 120° C., then 0.12 g (0.00055 mol) of tert-butyl perethylhexanoate are again added and the mixture is stirred for a further 60 min at 120° C. The excess diisopropyl phosphite and the solvent are distilled off under reduced pressure (applying a high vacuum). The crude product is purified by chromatography on silica gel (eluent: dichloromethane/methanol). 1.95 g (61.4% of theory) of L-3-benzyloxycarbonyl-4-[2-(diisopropoxyphosphinyl)ethyl]-1,3-oxazolidin-5-one are obtained as a colorless oil.

$^1$H-NMR (CDCl$_3$): 1.30 (d, J=6Hz, 12H), 1.47-2.45 (m, 4H), 4.36 (t, J=5.5Hz, 1H), 5.66 (m, 2H), 5.18 (s, 2H), 5.23 (d, J=5Hz, 1H), 5.53 (d, J=5Hz, 1H), 7.37 (s, 5H)

$^{31}$P-NMR (CDCl$_3$): 27.645

$[\alpha]_D^{21}$: 56.6° (C=0.59 in CHCl$_3$)

Starting from L-2-methyl-3-benzyloxycarbonyl-4-vinyl-1,3-oxazolidin-5-one, the following compounds of the formula IV can be obtained:

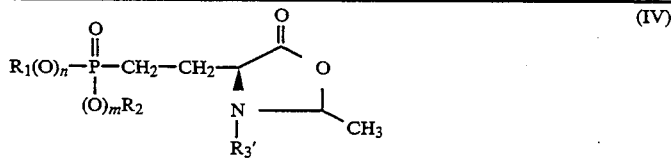

(IV)

| Example | R₁ | R₂ | R₃' | n | m | Yield | ³¹P-NMR [δ] | $[\alpha]_D^{21}$ |
|---|---|---|---|---|---|---|---|---|
| 7 | CH₃ | C₂H₅ | COOCH₂C₆H₅ | 0 | 1 | 77.4% | 52.645 53.008 | 58.8° (c = 0,41, CHCl₃) |
| 8 | CH(CH₃)₂ | CH(CH₃)₂ | COOCH₂C₆H₅ | 1 | 1 | 65.5% | 27.747 27.900 | 31,6° (c = 0,45, CHCl₃) |
| 9 | CH₃ | CH₃ | COOCH₂C₆H₅ | 0 | 0 | 34.7% | | |

B. Preparation of the Final Products (Process Step b))

EXAMPLE 10

L-Homoalanin-4-yl(methyl)phosphinic Acid Hydrochloride 1.84 g (0.0048 mol) of L-3-benzyloxycarbonyl-4-[2-[isobutoxy(methyl)phosphinyl]ethyl]-1,3-oxazolidin-5-one are taken up in 60 ml of 6N hydrochloric acid and the mixture is heated under reflux for 6 hours under a nitrogen atmosphere. The aqueous reaction mixture is extracted three times using 20 ml of dichloromethane each time, a little active carbon is added, the mixture is boiled for a short time and, after filtering off the active carbon, concentrated to dryness. The combined dichloromethane extracts are discarded. In this manner, 0.95 g (91.0% of theory) of L-homoalanin-4-yl(methyl)phosphinic acid hydrochloride is obtained as a slightly yellowish powder which is identified by its ¹H-NMR spectrum.

¹H-NMR (D₂O): 1.55 (d, J=14Hz, 3H), 1.71–2.43 (m, 4H), 4.16 (t, J=5.5Hz, 1H) The enantiomer excess, which was determined with the aid of an HPLC method [J. Chromatogr. 368, 413 (1986)], is 97.4% ee.

EXAMPLE 11

L-Homoalanin-4-yl(methyl)phosphinic Acid

Starting from L-2-methyl-3-benzyloxycarbonyl-4-[2-[ethoxy(methyl)phosphinyl]ethyl]-1,3-oxazolidin-5-one (Example 7), 91.1% of theory of L-homoalanin-4-yl(methyl)phosphinic acid hydrochloride having an enantiomer excess of 97.0% ee is obtained analogously to Example 10, and the product is converted into the free amino acid in a customary manner by reaction with about twice the molar amount of propene oxide.

¹H-NMR (D₂O)=1.38 (d, J=14Hz, 3H), 1.50–2.35 (m, 4H), 3.97 (t, J=5.5Hz, 1H)

M.p.=208°–211° C. (dec.)

$[\alpha]_D^{19}=16.1°$ (C=0.70 in H₂O)

This corresponds to an optical yield of at least 94.7%, relative to $[\alpha]_D^{23}=17.0°$ (c=1.00 in H₂O) for optically pure L-homoalanin-4-yl (methyl) phosphinic acid ( Sci. Reports of MeiJi Seika Kaisha 12, 42 (1973)).

EXAMPLE 12

L-2-Amino-4-phosphonobutyric Acid 1.15 g (0.0028 mol) of L-3-benzyloxycarbonyl-4-[2-(diisopropoxyphosphinyl)ethyl]-1,3-oxazolidin-5-one (Example 6) are dissolved in 25 ml of 6N hydrochloric acid and heated under reflux for 10 hours under a nitrogen atmosphere. The aqueous reaction mixture is extracted three times using 15 ml of dichloromethane each time, a little active carbon is added, the mixture is boiled for a short time and, after filtering off the active carbon, concentrated to dryness. The combined organic extracts are discarded. 0.52 g (84.6%) of L-2-amino-4-phosphonobutyric acid hydrochloride is obtained which solidifies as a glass-like solid which is taken up in 15 ml of ethanol/water. 0.24 g (46.8% of theory) of L-2-amino-4-phosphonobutyric acid is obtained by addition of 0.5 ml [=0.42 g (0.0072 mol)] of propene oxide.

¹H-NMR (D₂O): 1.50–2.37 (m, 4H), 4.00 (t, J=5.5Hz, 1H)

$[\alpha]_D^{20}$: 16.7 (C=0.55 in 6N HCl)

EXAMPLE 13

L-4-Dimethylphosphinyl-2-aminobutyric Acid Hydrochloride

Analogously to Example 12, 95.7% of theory of L-4-dimethylphosphinyl-2-aminobutyric acid hydrochloride which solidifies as a glass-like solid is obtained starting from L-3-benzyloxycarbonyl-4-[2-(dimethylphosphinyl)ethyl]-1,3-oxazolidin-5-one (Example 5).

$[\alpha]_D^{20}$: 15.0° (C=0.65 in 1N HCl)

EXAMPLE 14

Isobutyl L-(N-benzyloxycarbonyl)-homoalanin-4-yl(methyl)-phosphinate 2.10 g (0.0055 mol) of L-3-benzyloxycarbonyl-4-[2-[isobutoxy(methyl)phosphinyl]ethyl]-1,3-oxazolidin-5-one (Example 2) are dissolved in 11 ml of tetrahydrofuran and 11 ml of 1N sodium hydroxide solution are added. The mixture is stirred for 1 hour at room temperature and then concentrated in a water Jet vacuum. The residue is rendered acidic by addition of 11 ml of 1N hydrochloric acid and the aqueous solution is extracted three times using 20 ml of dichloromethane each time. The combined organic extracts are dried over sodium sulfate and concentrated to dryness. 1.62 g (79.3% of theory) of isobutyl L-(N-benzyloxycarbonyl)-homoalanin-4-yl(methyl)phosphinate are obtained which solidifies as a glass-like solid.

³¹P-NMR (CDCl₃): 58.550, 58.652

$[\alpha]_D^{19.5}$: 32.4° (C=1.06 in CHCl₃)

C₁₇H₂₆NO₆P (371.363) Calculated: C 55.0; H 7.1; N 3.8 Found: C 54.6; H 6.8; N 3.9

EXAMPLE 15

Isobutyl L-homoalanin-4-yl(methyl)phosphinate 1.00 g (0.0027 mol) of isobutyl L-(N-benzyloxycarbonyl)homoalanin-4-yl(methyl)phosphinate (Example 14) are dissolved in 25 ml of methanol, 0.1 g of palladium on active carbon (10%) is added and the mixture is hydrogenated at room temperature and a pressure of 3.0 bar for 24 h. After depressurizing the reaction vessel, the catalyst is filtered off and the filtrate is concentrated to dryness. 0.54 g (84.3% of theory) of isobutyl L-homoalanine-4-yl(methyl)phosphinate is obtained by taking up the residue in acetone/water.

M.p.: 183°–84° C. (dec.)

$^{31}$P-NMR (D$_2$O): 61.466

$[\alpha]_D^{21}$: 11.8° (C=1.06 in H$_2$O)

C$_9$H$_{20}$NO$_4$P (237.233) Calculated: C 45.6; H 8.5; N 5.9; Found: C 46.2; H 8.2; N 5.9

EXAMPLE 16

L-4-[Isobutoxy(methyl)phosphinyl]-2-[(benzyloxycarbonyl)-(hydroxymethyl)amino]butyryl-L-alanyl-L-alanine methyl ester 0.53 g (0.0025 mol) of L-alanyl-L-alanine methyl ester hydrochloride are suspended in 5 ml of tetrahydrofuran and 0.23 g (0.0022 mol) of triethylamine are added at −20° C. After stirring at −20° C. for 20 min, a solution of 0.86 g (0.0022 mol) of L-3-benzyloxycarbonyl-4-[2-[isobutoxy(methyl)phosphinyl] ethyl]-1,3-oxazolidin-5-one in 5 ml of tetrahydrofuran is added dropwise. The mixture is stirred at −20° C. for 30 min, then warmed to room temperature and subsequently stirred at 50° C. The precipitate which separates is filtered off and the filtrate is concentrated completely in a high vacuum. 1.10 g of a viscous oil is obtained which is taken up hot in toluene and filtered. After concentrating the filtrate in a high vacuum, 0.85 g (71.6% of theory) of L-4-[isobutoxy(methyl)phosphinyl]-2-[(benzyloxycarbonyl)(hydroxymethyl)amino]butyryl-L-alanyl-L-alanine methyl ester remain as a colorless oil.

$^1$H-NMR (d$_6$-DMSO): 0.86 (d, J=7 Hz, 6H), 1.28 (d, J=7 Hz, 3H), 1.32 (d, J=7 Hz, 3H), 1.36 (d, J=14 Hz, 3H), 1.10–2.22 (m, 5H), 3.62 (s, 3H), 3.63 (t, J=7 Hz, 2H), 4.27 (m, 3H), 4.84 (m, broad, 2H), 5.10 (s, 2H), 7.35 (s, 5H), 8.10 (s, broad, 1H), 8.35 (d, broad 7 Hz, 1H).

I claim:

1. A compound of the formula (IV)

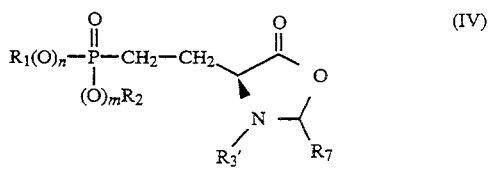

in which

R$_1$ and R$_2$, independently of one another, are hydrogen, (C$_1$–C$_6$)-alkyl which is unsubstituted, monosubstituted or polysubstituted by halogen or (C$_6$–C$_{10}$)-aryl, or are (C$_3$–C$_{10}$)cycloalkyl, R$_3$' is (C$_1$–C$_6$)-alkyl which is unsubstituted, monosubstituted or polysubstituted by halogen and monosubstituted by hydroxyl or which is monosubstituted by hydroxyl, or is (C$_1$–C$_{10}$)-acyl which can be monosubstituted or polysubstituted by halogen or (C$_1$–C$_6$)-alkyl, or can be monosubstituted by (C$_6$–C$_{10}$)-aryl, (C$_1$–C$_6$)-alkoxy or (C$_1$–C$_6$)-alkoxy which is substituted by (C$_6$–C$_{13}$)-aryl, R$_7$ is hydrogen, (C$_1$–C$_3$)-alkyl which can be monosubstituted or polysubstituted by halogen, n is the number 0 or 1, with the exception that R$_1$ is not hydrogen if n is 1, and m is the number 0 if R$_2$ is not hydrogen, or is 1.

2. A compound of the formula (IV) as claimed in claim 1, wherein

R$_3$' is dichloroacetyl, trichloroacetyl, trifluoroacetyl, benzyloxycarbonyl, fluorenylmethoxycarbonyl or naphthylmethoxycarbonyl.

3. A compound of the formula (IV) as claimed in claim 1, wherein R$_3$' is benzyloxycarbonyl.

4. A compound of the formula (IV) as claimed in claim 1, wherein

R$_1$(O)$_n$ is methyl, ethyl, isopropyl, cyclohexyloxy, methoxy, ethoxy or isopropoxy, and R$_2$(O)$_m$ is methyl, ethyl, isopropyl, cyclohexyloxy, methoxy, ethoxy, isopropoxy or hydroxyl.

5. A compound of the formula (IV) as claimed in claim 4, wherein R$_3$' is benzyloxycarbonyl.

* * * * *